US007955479B2

(12) United States Patent
Vanier

(10) Patent No.: US 7,955,479 B2
(45) Date of Patent: Jun. 7, 2011

(54) METHOD AND APPARATUS FOR CONDUCTING MICROWAVE ASSISTED ORGANIC REACTIONS WITH GAS-PHASE REACTANTS

(75) Inventor: Grace S. Vanier, Indian Trail, NC (US)

(73) Assignee: CEM Corporation, Matthews, NC (US)

( * ) Notice: Subject to any disclaimer, the term of this patent is extended or adjusted under 35 U.S.C. 154(b) by 989 days.

(21) Appl. No.: 11/370,139

(22) Filed: Mar. 7, 2006

(65) Prior Publication Data

US 2007/0209924 A1 Sep. 13, 2007

(51) Int. Cl.
C07C 1/00 (2006.01)
C07F 1/00 (2006.01)
(52) U.S. Cl. .................... 204/157.15; 204/157.6
(58) Field of Classification Search .............. 204/157.15, 204/157.6
See application file for complete search history.

(56) References Cited

U.S. PATENT DOCUMENTS

| | | | |
|---|---|---|---|
| 2,843,589 A * | 7/1958 | Scigliano | 544/358 |
| 3,926,556 A | 12/1975 | Boucher | |
| 4,736,083 A | 4/1988 | Saville | |
| 5,369,034 A * | 11/1994 | Hargett et al. | 436/155 |
| 5,451,302 A | 9/1995 | Cha | |
| 6,054,695 A | 4/2000 | Lautenschlager | |
| 6,258,329 B1 | 7/2001 | Mutterer, Jr. et al. | |
| 6,288,379 B1 | 9/2001 | Greene et al. | |
| 6,592,723 B2 | 7/2003 | Cha | |
| 6,603,021 B2 * | 8/2003 | Werpy et al. | 548/552 |
| 6,720,540 B2 | 4/2004 | Fagrell | |
| 6,744,024 B1 * | 6/2004 | Hayes et al. | 219/679 |
| 6,759,025 B2 | 7/2004 | Hong et al. | |
| 2005/0121307 A1 | 6/2005 | Hargett et al. | |
| 2006/0039838 A1 | 2/2006 | Barnhardt et al. | |
| 2006/0137613 A1 * | 6/2006 | Kasai | 118/723 MW |

FOREIGN PATENT DOCUMENTS

| | | |
|---|---|---|
| DE | 102004041492 A1 | 3/2006 |
| WO | 2004002617 A | 1/2004 |
| WO | WO 2004073363 A1 * | 8/2004 |

OTHER PUBLICATIONS

Bonnet et al., "Study of the Thermal Repartition in a Microwave Reactor: Application to the Nitrobenzene Hydrogenation", Chemical Engineering and Processing, vol. 43 (no month, 2004), pp. 1435-1440.*
Lidstrom et al., "Microwave Assisted Organic Synthesis—A Review", Tetrahedron, vol. 57 (no month, 2001), pp. 9225-9283.*
Simmonds et al., "Novel Type of Hydrogenator", Analytical Chemistry (Jul. 1972), vol. 44, No. 8, pp. 1548-1550.*
Jones et al., "Continuous-Flow High Pressure Hydrogenation Reactor for Optimization and High-Throughput Synthesis", J. Comb. Chem. (no month, 2006), vol. 8, pp. 110-116.*

(Continued)

Primary Examiner — Edna Wong
(74) Attorney, Agent, or Firm — Summa, Additon & Ashe, P.A.

(57) ABSTRACT

A method of accelerating the hydrogenation of organic compounds is provided. The method includes positioning an microwave transparent reaction vessel containing at least one reactant suitable for hydrogenation in a microwave cavity, purging the reaction vessel, charging the reaction vessel with hydrogen gas, and applying a continuous single mode of microwave radiation within the cavity and to the vessel and its contents for a time sufficient to effect a chemical change in the reactants.

12 Claims, 1 Drawing Sheet

OTHER PUBLICATIONS

A. Kramer et al, "Synthesis and Screening of Peptide Libraries on Continuous Cellulose Membrane Supports"; Methods in Molecular Biology, vol. 87: Combinatorial Peptide Library Protocols; Humana Press, Inc.; Totowa, NJ; pp. 25-39.

Heller et al, "Microwave-enhanced hydrogenations at medium pressure suing a newly constructed reactor," Tetrahedron Letters 46 (Jan. 2005), pp. 1247-1249.

Banik et al, "Microwave-Assisted Rapid and Simplified Hydrogenation," J. Org. Chem. (1999), vol. 64, No. 16, pp. 5746-5753.

International Search Report for PCT/US2007/005931; Authorized Officer: Seufert, Gudrun; Mailed Sep. 11, 2007; 3 pages.

Bonnet C et al: "Study of thermal repartition in a microwave reactor: application to the nitrobenzene hydrogenation," Chemical Enginnering and Processing, vol. 43, No. 11, Nov. 2004, pp. 1435-1440.

Conde L D et al: "Oligomerization of methane via microwave heating using Raney nickel catalyst," Journal of Catalysis, vol. 218, No. 1, Aug. 15, 2003, pp. 201-208.

Evalueserve: "Developments in Microwave Chemistry," Internet article online 2005, retrieved from URL:http//www.rsc.org/images/evaluserve_tcm18-16758.pdf; retrieved Aug. 20, 2007.

Toukoniitty et al, "Ethyl pyruvate hydrogenation under microwave irradiation," Chemical Engineering Journal, vol. 126, No. 2-3, Feb. 7, 2007, pp. 103-109.

* cited by examiner

METHOD AND APPARATUS FOR CONDUCTING MICROWAVE ASSISTED ORGANIC REACTIONS WITH GAS-PHASE REACTANTS

BACKGROUND

The present invention relates generally to the field of microwave-assisted chemistry, and in particular relates to microwave-assisted hydrogenation reactions.

A number of microwave-assisted chemistry techniques are known in the academic and commercial arenas. Microwaves have some significant advantages in heating (or otherwise supplying energy to) certain substances. In particular, when microwaves interact with substances with which they can couple, most typically polar molecules or ionic species, the microwaves can immediately create a large amount of kinetic energy in such species, which can provide sufficient energy to initiate or accelerate various chemical reactions. Microwaves also have an advantage over conduction heating in that the surroundings do not need to be heated because the microwaves can react instantaneously with the desired species.

The term "microwaves" refers to that portion of the electromagnetic spectrum between about 300 and 300,000 megahertz (MHz) with wavelengths of between about one millimeter (1 mm) and one meter (1 m). These are, of course, arbitrary boundaries, but help quantify microwaves as falling below the frequencies of infrared (IR) radiation and above those referred to as radio frequencies. Similarly, given the well-established inverse relationship between frequency and wavelength, microwaves have wavelengths longer than infrared radiation, but shorter than radio frequency wavelengths.

Because of their wavelength and energy, microwaves have been historically most useful in driving robust reactions or reactions in relatively large sample amounts, or both. Stated differently, the wavelengths of most microwaves tend to create multi-mode situations in cavities in which the microwaves are being applied. In a number of types of chemical reactions, this offers little or no disadvantage, and microwave techniques are commercially well established for reactions such as digestion or loss-on-drying moisture content analysis.

Relatively robust, multi-mode microwave techniques, however, tend to be less successful when applied to small samples of materials. Although some chemistry techniques have the obvious goal of scaling up a chemical reaction, in many laboratory and research techniques, it is often necessary or advantageous to carry out chemical reactions on small samples. For example, the availability of some compounds may be limited to small samples. In other cases, the cost of reactants may discourage large sample sizes. Other techniques, such as combinatorial chemistry, use large numbers of small samples to rapidly gather a significant amount of information, and then tailor the results to provide the desired answers, such as preferred candidates for pharmaceutical compounds or their useful precursors.

Microwave devices with larger, multimode cavities that are suitable for other types of microwave-assisted techniques (e.g., drying, digestion, etc.) are generally less-suitable for smaller organic samples because the power density pattern in the cavity is relatively non-uniform.

Accordingly, the need for more focused approaches to microwave-assisted chemistry has led to improvements in devices for this purpose. For example, in the commercially available devices sold under the assignee's (CEM Corporation, 3100 Smith Farm Road, Matthews, N.C. 28106) DISCOVER®, EXPLORER®, VOYAGER®, NAVIGATOR™, LIBERTY™, and INVESTIGATOR™ trademarks have provided single mode focused microwave devices that are suitable for small samples and for sophisticated reactions such as chemical synthesis.

The very success of such single mode devices has, however, created associated problems. In particular, the improvement in power density provided by single-mode devices can cause significant heating in small samples, including undesired over-heating in some circumstances. Such over-heating can raise derivative problems when one or more of the reactants are in the gas phase. Hydrogenation represents one such reaction.

As is known to those having ordinary skill in the art, alkenes typically react in the presence of hydrogen ($H_2$) and a catalyst to form alkanes. This reaction is known as a hydrogenation reaction. A common hydrogenation is the hardening of animal fats or vegetable oils to make them solid at room temperature and improve their stability. Hydrogen is added (in the presence of a catalyst) to carbon-carbon double bonds in the unsaturated fatty acid portion of the fat or oil molecule: Hydrogenation reactions are also important in petroleum refining; production of gasoline by cracking involves destructive hydrogenation (hydrogenolysis), in which large molecules are broken down to smaller ones and reacted with hydrogen.

Organic reactions that include a gas phase are known in the art as often lengthy and dangerous, with high potential for hydrogen gas explosions. One reason for the difficulty in conducting (e.g.) hydrogenation reactions is the necessity of working with hydrogen gas. As is known to those having ordinary skill in the art, hydrogen gas is most often stored under pressure and is a highly flammable gas. This high flammability renders hydrogen gas an undesirable reagent in lengthy reactions.

Traditional hydrogenation reactions are typically conducted at atmospheric pressure in a hydrogen atmosphere. The hydrogen atmosphere may often be provided by attaching a balloon filled with hydrogen to a round bottom flask containing the hydrogenation reactants.

Catalyst-assisted hydrogenation is also frequently carried out in a shaker-type apparatus at pressures of up to about five atmospheres and temperatures up to about 80° C. Hydrogenation instruments available from Parr Instrument Company, Moline, Ill., USA are illustrative of such techniques and represent a basic design (albeit with improvements, accessories and related enhancements) that originated in the 1920s. According to Parr, "Materials to be treated . . . are sealed in a reaction bottle with a catalyst and connected to a hydrogen reservoir. Air is removed either by evacuating the bottle or by flushing with hydrogen. Pressure is then applied from the reservoir and the bottle is shaken vigorously to initiate the reaction. The bottle can be heated or cooled during this process, if necessary. After the reaction reaches the desired point, the shaker is stopped, the bottle vented and the product and catalyst are recovered." (www.parrinstruments.com).

Hydrogenation reactions of this sort usually have a slow reaction rate and poor reaction yields. For example, a typical hydrogenation of cholesterol takes approximately twenty four hours and evidences a yield of less than about 70%.

The lengthy reaction times, such as those described above, may subject the researcher to extended exposure to pressurized hydrogen gas, therefore creating more opportunities for problems with the hydrogen gas. Additionally, reactions with such extended reaction times are difficult to monitor continuously.

Previous attempts to utilize microwave technology for hydrogenation reactions to reduce reaction time and hydrogen gas exposure typically focused on transfer hydrogenation. "Transfer" reactions refer to hydrogenation reactions performed by producing hydrogen gas in situ rather than working with hydrogen gas maintained under pressure. A common technique for the in situ production of hydrogen gas utilizes formic acid. This technique often suffers from the drawbacks of extended reaction times and low yields.

Another technique for conducting microwave assisted hydrogenation reactions, disclosed by Heller et al in *Tetrahedron Letters* 46 (2005) 1247, utilizes hydrogen gas at a pressure of about 25 bar (i.e., a saturated system), a temperature of about 125° C., and a reaction time of about one hour to hydrogenate pyridine-2-carboxylic acid to give pipecoloic acid. The reaction included a minimum volume of about 20 mL and a maximum volume of about 200 mL. Similarly, hydrogenation of piperdinium utilizing the Heller method proceeded at 20 bar, 60° C., for 1.5 hours; debenzylation typically required a reaction time of about two hours, azide hydrogenation typically required a reaction time of about three hours; and hydrogenation of strychnine typically lasted about two hours.

Although this technique resulted in reduced reaction times, the necessary pressures increase the possibility of hydrogen gas explosions in the lab. Additionally, the reactions times of greater than one hour also increase the possibility of hydrogen gas explosions.

SUMMARY

In one aspect, the invention is a method of accelerating the hydrogenation of organic compounds. The method includes positioning an microwave transparent reaction vessel containing at least one reactant suitable for hydrogenation in a microwave cavity, purging the reaction vessel, charging the reaction vessel with hydrogen gas, and applying a continuous single mode of microwave radiation within the cavity and to the vessel and its contents for a time sufficient to effect a chemical change in the reactants.

In another aspect, the invention is a method of accelerating the hydrogenation of organic compounds including positioning a microwave transparent reaction vessel containing hydrogenation reactants in a microwave cavity, purging the reaction vessel, charging the reaction vessel with hydrogen gas, and applying a continuous single mode of microwave radiation within the cavity and to the vessel and its contents at a temperature sufficient to effect a chemical change in the reactants.

In yet another aspect, the invention is an instrument for conducting microwave assisted hydrogenation reactions including a source for applying a continuous single mode of microwave radiation within a microwave cavity and to a microwave-transparent vessel and its contents in the cavity. The instrument further includes means for charging the vessel with hydrogen gas and at least one vent for venting the vessel.

In another aspect, the invention is an improvement in a method of carrying out hydrogenation reactions. The improvement includes charging a reaction vessel containing hydrogenation reactants with hydrogen gas and applying a continuous single mode of microwave radiation to the reaction vessel and its contents inside a microwave cavity and at a temperature and for a time sufficient to effect a hydrogenation reaction.

The foregoing and other aspects and embodiments of the invention will become clearer based on the following detailed description taken in conjunction with the accompanying drawing.

BRIEF DESCRIPTION OF THE DRAWING

The present invention now will be described more fully hereinafter with reference to the accompanying drawing, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements.

DETAILED DESCRIPTION

Figure 1:
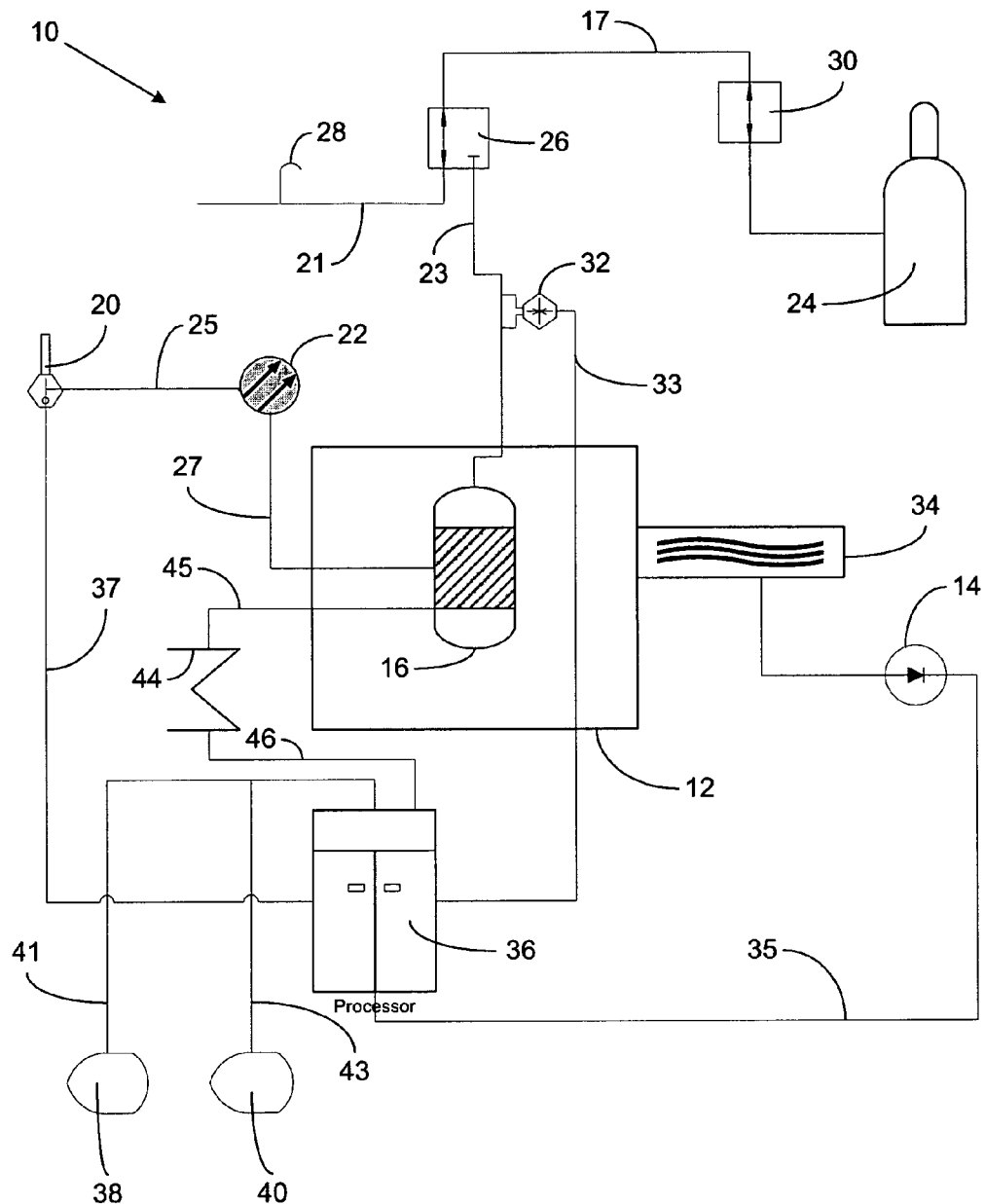
FIG. 1 is a schematic diagram of the elements of an instrument in accordance with one embodiment of the invention.

The present invention is a method and apparatus for conducting microwave assisted chemical reactions with a gasphase reactant, such as microwave assisted hydrogenation reactions. Microwave assisted hydrogenation reactions may provide higher yields, safer reactions, and shorter reaction times than conventional methods of conducting hydrogenation reactions. Thus, hydrogenation as described herein provides a helpful, rather than limiting, illustration of the invention.

Unless otherwise defined, all terms (including technical and scientific terms) used herein have the same meaning as commonly understood by one having ordinary skill in the art to which this invention belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

In describing the invention, it will be understood that a number of techniques and steps are disclosed. Each of these has individual benefit and each can also be used in conjunction with one or more, or in some cases all, of the other disclosed techniques. Accordingly, for the sake of clarity, this description will refrain from repeating every possible combination of the individual steps in an unnecessary fashion. Nevertheless, the specification and claims should be read with the understanding that such combinations are entirely within the scope of the invention and the claims.

FIG. 1 is a schematic diagram of one aspect of the invention. According to this aspect, the invention is an instrument broadly designated at 10 for conducting microwave assisted chemical reactions. The instrument 10 includes a microwave cavity 12, preferably a closed microwave cavity, for conducting microwave assisted chemical reactions. In exemplary embodiments, the microwave cavity 12 is a substantially cylindrical cavity that supports a single mode at wavelengths generated by the relevant source.

The instrument 10 further includes a source, illustrated as the diode 14 for applying microwave radiation within the cavity 12 and to a vessel 16 and its contents. The apparatus may also include a waveguide 34 in communication with the source and the cavity to direct the microwave radiation in the desired orientation. The apparatus also includes temperature monitoring means 20 for monitoring the temperature of the vessel 16 and its contents. The temperature monitoring means may include a fiber optic sensor 22 as depicted in FIG. 1. In exemplary embodiments, the temperature monitoring means is selected from one or more of thermometers, thermocouples, pyrometers, and optical temperature detectors.

It will be understood, of course, that although FIG. 1 illustrates these elements separately for purposes of clarity, a single fiber optic line could be used to carry both the illumination wavelengths from the source to the cavity as well as providing visible access for observation purposes. Accordingly, FIG. 1 is descriptive and exemplary rather than limiting of this and other aspects of the invention.

The instrument 10 may also include means for charging the vessel with hydrogen gas. In the illustrated embodiment, the charging means includes hydrogen gas tank 24. Other means known in the art for charging a reaction vessel with hydrogen gas are also contemplated as being useful in accordance with the present invention.

In one exemplary embodiment, the instrument 10 may also include at least one valve 26 between the charging means 24 and the vessel 16 for controlling the flow of hydrogen gas into the vessel 16. The instrument 10 may also include a vent 28 for venting the vessel 16. In one embodiment, the valve 26 may enable both charging and venting of the vessel 16.

In an exemplary embodiment, a shut-off valve 30 may be situated at or near the tank 24 to enable direct control of the hydrogen pressure between the tank 24 and the vessel 16. Such direct control may be desirable as an additional safety measure. As discussed previously, those having ordinary skill in the art will recognize the inherent difficulties in working with hydrogen gas. Accordingly, additional safety measures, such as the presently discussed shut-off valve 30, are often desirable.

In order to carry out the reaction appropriately and successfully, the valves 26 and 30 provide, individually, collectively, or redundantly, the ability to regulate the pressure, and thus the amount, of hydrogen from the source tank 24. Similarly, the vessel 16 must be capable of handling the pressures necessary to drive stoichiometric reactions to near-completion or completion.

In another embodiment, the instrument 10 can include a pressure sensor 32. The pressure sensor 32 may be in communication with the vessel 16 and its contents to monitor the pressure of a hydrogenation reaction. The schematic view of FIG. 1 illustrates the pressure sensor 32 as outside of the cavity and spaced from the valves 26,30, but it will be understood that this location is exemplary rather than limiting of the invention.

In one embodiment, the source 14 propagates a continuous single mode of microwave radiation in the cavity 12. Because of the nature of microwaves, which follow well understood laws of wave propagation, the production of a single mode is most often accomplished by designing a cavity 12 having a geometry that supports a single mode at a wavelength produced by the source 14. For example, in the United States, 2450 megahertz (MHz) is one of the regulated frequencies (wavelengths) reserved for laboratory microwave use. As used herein and generally well-understood in this field, the term "mode" refers to the permitted (i.e., with respect to principles of physics) electromagnetic field pattern within a cavity.

Microwave modes are generally referred to by the $TE_{n,l,m}$ designation (TE for the magnetic field) where the subscripts refer to the number of nulls in the propagated direction. Cavities 12 that can support single modes are set forth in the art and are generally understood by those familiar with microwaves and their propagations. An exemplary cavity 12 for propagating a single mode of microwave radiation is set forth in U.S. Pat. No. 6,288,379, incorporated herein by reference.

Any appropriate microwave source 14 can be used that is consistent with the other aspects of the invention. Typical sources such as magnetrons, klystrons, or solid state sources, such as Gunn diodes, can be used in the present invention. In an exemplary embodiment, the application of continuous microwave radiation is accomplished using a resonant inverter switching power supply as set forth in previously incorporated U.S. Pat. No. 6,288,379. Thus, the term "continuous" is used herein in a descriptive rather than an absolute sense and refers to applying radiation from a source while driving the source at a frequency greater than about 60 hertz. More preferably, the source is driven at a frequency greater than about 600 hertz, even more preferably at greater than about 6000 hertz, and most preferably at frequencies between about 10,000 and about 250,000 hertz. As described in the '379 patent, this permits the power to be applied at a more even level over a longer period of time than in conventional devices which operate on 50 cycle (typical in Europe) or 60 cycle alternating current (standard in the United States).

FIG. 1 also illustrates a cooling mechanism schematically illustrated as the coil 44. In preferred embodiments the cooling system is the same as or equivalent to those described in commonly assigned U.S. Pat. No. 6,744,024 and co-pending and commonly assigned United States Patent Application Publication No. 20060039838. The cooling mechanism moderates or controls the temperature in the vessel during the application of microwave energy. The physical connection between the coil (or equivalent cooling mechanism) 44 and the vessel 16 is schematically illustrated by the line 45, and the coil (or equivalent) 44 is in signal communication with the processor 36 through the line 46. For purposes of clarity, FIG. 1 illustrates the coil 44 as outside of the cavity 12, and this will normally be the position in order to avoid interference between metal parts and the single mode in the cavity 12. Thus, the line 45 will typically be formed of a microwave transparent material that can carry cooling air or other fluid without interfering with the wave mode in the cavity 12. The external location of the coil 44 is, however, an exemplary description rather than limiting one.

The invention may further include a processor 36 in signal communication with one or both of the temperature sensor 20 and the pressure sensor 32. The processor 36 can be selected from among widely available and well understood processors such as the Pentium® or Core™ Duo series from Intel® (Santa Clara, Calif.) that are commonly used in personal computers, or functionally equivalent processors from other sources such as AMD® (Sunnyvale, Calif.). In some cases, a commercially-available desktop or laptop computer can be programmed with software to carry out the desired control functions while in other circumstances, the processor can be used in cooperation with preprogrammed read only memory (ROM) for the same purpose. In either case, the skilled person can obtain and use the relevant processor without undue experimentation. General discussions of control circuits and logic and related devices and systems are widely available, with one common source being Dorf, *The Electrical Engineering Handbook,* 2d Ed. (1997, CRC Press), at pages 1104-1107, sections 43.6-43.7.

In one exemplary embodiment, the apparatus may also include a temperature display 38 to further enable monitoring of the temperature of the reaction. The apparatus may further include a pressure display 40 to further enable monitoring of the pressure of the reaction.

In another exemplary embodiment, the processor 36 is in signal communication with the temperature sensor 20 and is capable of controlling the microwave source 14 in response to the monitored temperature.

In another exemplary embodiment, the processor 36 is in signal communication with the pressure sensor 32 for controlling the microwave source 14 in response to the monitored pressure.

Stated differently, the processor 36 may be programmed to reduce or strengthen the output of the microwave source 14 in response to a monitored change in the temperature and/or pressure of the vessel 16 and its contents. Accordingly, the source 14 may be automatically shut-off or adjusted in response to the monitored temperature and/or pressure. In one embodiment, the processor 36 may be programmed to adjust the microwave source 14 when the temperature and/or pressure reach a threshold level.

Although the term "vessel" is used herein with respect to both the instrument and method aspects of the invention, it will be understood that the invention is not limited to vessels of any particular size or shape. Additionally, the term vessel can include other physical arrangements for handling the reactants, including flow-through systems. In general, because the hydrogenation reaction typically incorporates hydrogen gas as one of the reactants, the vessel or vessels system will be sealed to contain the hydrogen gas with the other reactants. The most typical method of containing the hydrogen gas is to use a sealed vessel, but an open vessel in a larger sealed system or some other equivalent arrangement, could be incorporated provided it operated consistently with the remainder of the method steps described herein. As noted elsewhere herein, the vessel should be able to withstand expected pressures (usually up to several atmospheres) at elevated temperatures (usually up to about 200° C.). Exemplary vessels are well-understood in the microwave art such as those available from the assignee herein.

FIG. 1 also includes a number of schematically illustrated pathways, some (i.e. pipes or tubing) for gas flow communication, some (wires or wireless devices) for electrical or signal communication, and some (fiber optics) for optical communication. Thus, the line designated at 17 represents a gas flow path from the hydrogen tank 24 through the valve 30 to the valve 26. A similar gas flow pipe 21 communicates between the vent 28 and the valve 26. A third gas flow pipe 23 communicates between the valve 26 and the vessel 16. Optical lines 25 and 27 communicate between the vessel 16 and the temperature monitor 20. Electrical or signal lines respectively communicate between the pressure sensor 32 and the processor 36 (line 33), between the processor 36 and the source 14 (line 35), between the processor 36 and the temperature sensor 20 (line 37), between the processor 36 and the display 38 (line 41), and between the processor 36 and the display 40 (line 43).

In another aspect, the invention is a method of accelerating the organic reactions that include a gas phase reactant. In terms of hydrogenation, the method includes positioning a microwave transparent reaction vessel containing at least one reactant suitable for hydrogenation in a microwave cavity. The reaction vessel may be purged, either before or after the positioning step, and then charged with hydrogen gas. After the vessel is positioned in the cavity, the method further includes applying a continuous single mode of microwave radiation within the cavity and to the vessel and its contents until the reactant is hydrogenated to a desired yield.

As used herein, the term "purging," refers to any appropriate step of emptying undesired gases from the reaction vessel and replacing them with the desired reactant gas (or gases), usually hydrogen. In some cases the purging step empties (or almost empties) the vessel of gas using a vacuum type pump while in other cases, the purging gas is added in a manner that displaces other gases so that only the desired purging gas or reactant gas remains.

Those having ordinary skill in the art will recognize that a hydrogenation reaction is an addition reaction, during which on atom of hydrogen adds to each atom in a double bond. For example, one atom of hydrogen may add to each carbon atom in a carbon-carbon double bond.

Reactants suitable for hydrogenation include those reactants having double or triple bonds. Accordingly, common hydrogenation reactants are often alkenes or alkynes. Other reactants including double bonds, such as between a carbon atom and a nitrogen atom, are also contemplated as useful in the present invention. Those having ordinary skill in the art will recognize, therefore, useful hydrogenation reactants.

In one embodiment, the step of positioning a microwave transparent reaction vessel containing hydrogenation reactants in a microwave cavity includes positioning a microwave transparent vessel further containing at least one hydrogenation catalyst. As is known to those having ordinary skill in the art, common hydrogenation catalysts include, but are not limited to, platinum, nickel, palladium, rhodium, ruthenium, and combinations thereof. Other hydrogenation catalysts known in the art are also contemplated as useful in the present invention.

In another embodiment, the method includes placing reactants in a microwave-transparent vessel, potentially, but not necessarily, including placing the reactants in pressure-resistant vessels which can be sealed prior to the application of microwave radiation. The vessel and its contents are then placed into a microwave cavity and microwave radiation, preferably a continuous single mode of microwave radiation, is applied within the cavity to the vessel and its contents while concurrently externally cooling the vessel.

In one embodiment, the step of purging the reaction vessel may be conducted more than once to further ensure the purity of the vessel atmosphere. For example, the reaction vessel may be purged and charged with hydrogen two or more times before the application of microwave radiation within the cavity.

In one embodiment, the step of charging the reaction vessel with hydrogen gas may include charging the reaction vessel with an amount of hydrogen gas that is stoichiometric with respect to the at least one hydrogenation reactant. For example, the reaction vessel may be charged with a sufficient amount of hydrogen gas such that the ratio of double bonds to be hydrogenated to $H_2$ is about 1:1.

The determination of desired or appropriate stoichiometric amounts is well within the skill of persons familiar with this art. As well understood, the stoichiometric amount of a solid or liquid reactant is typically evaluated based on grams and molecular weight or (e.g. liquids) density, volume and molecular weight. For gases, amounts are calculated using the ideal gas law or well-understood derivations of the ideal gas law. Accordingly, once the volume of a vessel is defined or measured, the amount of gas in the vessel is directly proportional to the pressure.

In another embodiment, the step of charging the reaction vessel with hydrogen gas may include charging the reaction vessel with an amount of hydrogen gas that is greater than stoichiometric with respect to the at least one hydrogenation reactant. Stated differently, the reaction vessel may be charged with hydrogen gas such that the ratio of double bonds to be hydrogenated to $H_2$ is less than 1:1.

In yet another embodiment, where only partial hydrogenation of the reactants is desired, the reaction vessel may be charged with an amount of hydrogen gas that is less than stoichiometric with respect to the at least one hydrogenation reactant. For example, the reaction vessel may be charged with a sufficient amount of hydrogen gas such that the ratio of double bonds to be hydrogenated to $H_2$ is greater than about 1:1.

The present method may further include the step of monitoring the temperature of the reaction vessel. The temperature monitoring step may be conducted utilizing a temperature probe or other temperature monitoring means known in the art.

The method typically comprises heating the vessel and its contents to a temperature of between about 60 and 180° C., with the upper limit being represented by the temperature and pressure capacity of the vessel 16. In most circumstances, the vessel will withstand the necessary pressure at temperatures up to about 200° C. More robust vessels can, of course, be used, but at a certain point, the increase in temperature will drive degradation reactions rather than the desired hydrogenation. Thus the upper temperature and pressure limits are most often established by the reactants and the products rather than by the physical limits of the instrument or the vessel.

In one embodiment, the step of applying a continuous single mode of microwave radiation may include applying a continuous single mode of microwave radiation within the cavity and to the vessel and its contents for a time sufficient to effect a yield of greater than about 50% hydrogenation, more preferably greater than about 75% hydrogenation, and most preferably greater than about 90% hydrogenation. In one exemplary embodiment, the step of applying a continuous single mode of microwave radiation within the cavity includes applying a continuous single mode of microwave radiation within the cavity and to the vessel and its contents for a time sufficient to effect a yield of about 100% hydrogenation.

In at least one embodiment, the step of applying a continuous single mode of microwave radiation for a time sufficient to effect a chemical change in the reactants may include applying a continuous single mode of microwave radiation for between about two and twenty-five minutes.

In another embodiment, the method includes applying the continuous single mode of microwave radiation within the cavity and to the vessel and its contents to produce a temperature sufficient to hydrogenate the reactants to the desired yield. In one embodiment, the step of applying a continuous single mode of microwave radiation at a temperature sufficient to effect a chemical change includes heating, by utilizing the continuous single mode of microwave radiation, the vessel contents to a temperature of between about 60 and 180° C.

The method may also include the step of using various robotic transfers to both place the reactants in a microwave transparent vessel and to place the vessel and contents into a microwave cavity.

The invention provides the capability to moderate the microwave radiation in response to an observed change, either automatically or manually. The microwave radiation may be moderated in response to a monitored temperature change, a visually monitored change, or both. Additionally, it may be preferable to moderate the microwave radiation, either automatically or manually, in response to a predetermined monitored change.

In one aspect, the invention is a method of carrying out microwave assisted hydrogenation reactions. The method includes placing hydrogenation compositions—frequently reactants—in a microwave-transparent vessel, positioning the vessel and its contents inside a microwave cavity, and applying a continuous single mode of microwave radiation within the cavity and to the vessel and its contents It will be understood, of course, that although the term "reactants" is used frequently herein, the method is not limited to starting materials, but can be applied to any appropriate compositions.

In one embodiment, the microwave power may be adjusted either manually or automatically in response to the monitored change in the reactants in the vessel. Moreover, the microwave power may be adjusted in response to a change monitored by the temperature sensor or in response to a change monitored by a pressure sensor.

The method may also include placing the reactants in a vessel, preferably a pressure-resistant vessel, and sealing the vessel prior to the step of applying the microwave radiation. The step of applying microwave radiation preferably includes applying a continuous single mode of microwave radiation as previously discussed.

In another aspect, the invention is an improvement in a method of carrying out hydrogenation reactions. The improvement includes charging a reaction vessel containing hydrogenation reactants with hydrogen gas and applying a continuous single mode of microwave radiation to the reaction vessel and its contents at a temperature and for a time sufficient to effect a hydrogenation reaction.

In one embodiment, the method may further include catalyzing the hydrogenation reaction. Exemplary catalysts include nickel (Ni), platinum (Pt), palladium (Pd) and other noble metals and combinations of metals. Additionally, a variety of suitable hydrogenation catalysts are known to, and will be recognized by, those having ordinary skill in the art without undue experimentation.

The method may also include the step of purging the reaction vessel at least one time prior to the step of charging the reaction vessel with hydrogen gas.

The step of applying a continuous single mode of microwave radiation may include applying a continuous single mode of microwave radiation at a temperature between about 60 and 180° C., more preferably between about 65 and 85° C. The step of applying a continuous single mode of microwave radiation may further include applying a continuous single mode of microwave radiation for a time of between about two and twenty-five minutes.

The method may further include monitoring the temperature of the hydrogenation reaction and adjusting the microwave power, either automatically or manually, in response to a monitored temperature change. Similarly, the method may also include monitoring the pressure of the hydrogenation reaction and adjusting the microwave power in response to a monitored pressure change.

The present instrument and method provides a more efficient path for conducting hydrogenation reactions. The present method reduces the reaction time and increases the yield over both conventional hydrogenation techniques and previously developed microwave assisted hydrogenation techniques. Moreover, the present method provides improved safety when working with explosive hydrogen gas due to the reduced temperatures and exposure time to the hydrogen gas.

EXAMPLES

A number of hydrogenation reactions were conducted using the present apparatus and method. Several of these reactions, along with their reaction conditions and yields, are listed below. Unless otherwise noted, each reaction proceeded with a stoichiometric amount of hydrogen with respect to the reactant to be hydrogenated and 1% catalyst loading.

As used in the drawings, the abbreviation Pd/C refers to a palladium metal catalyst on a carbon support. The abbreviation EtOH refers to ethyl alcohol and the abbreviation EtOAc refers to ethyl acetate. The abbreviation $\mu\lambda$ refers to the application of microwaves. Simultaneous cooling was carried out using the PowerMAX™ single mode capacity microwave instrument available from the assignee herein, CEM Corporation of Matthews, N.C., USA.

Olefin Hydrogenation:
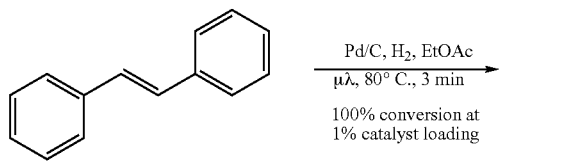
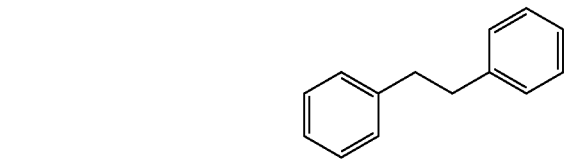
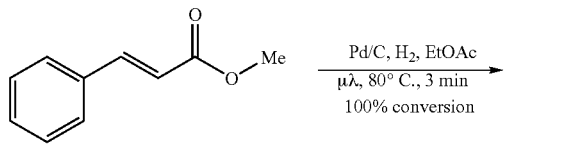
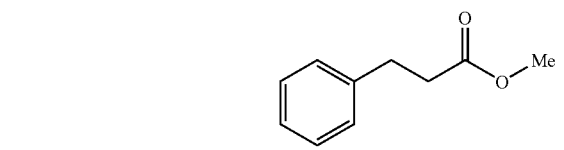
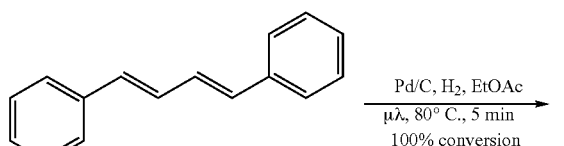
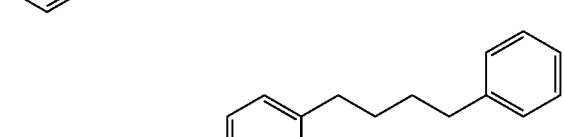
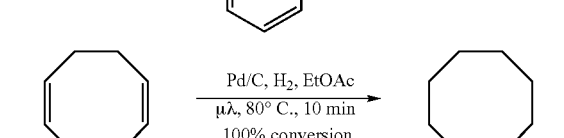
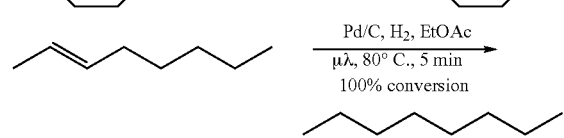
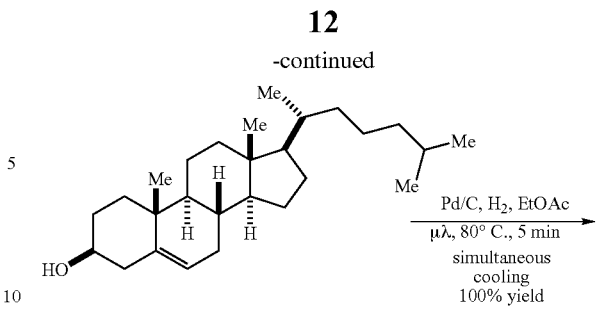
Alkyne Hydrogenation:
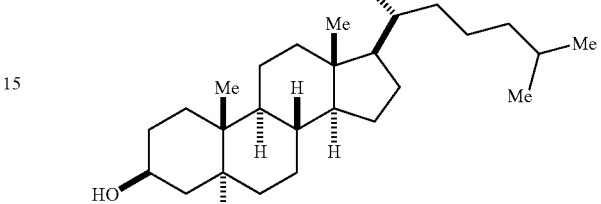
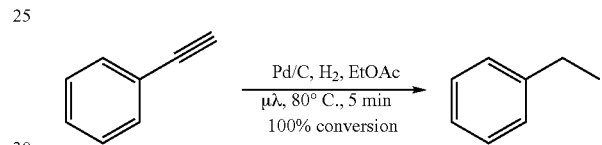
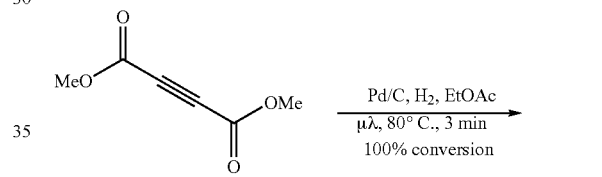
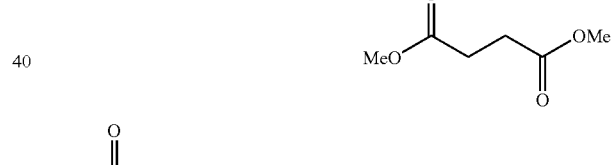
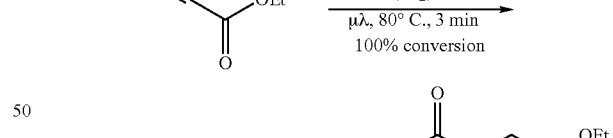
Reduction of Nitro Groups to Amine Groups:
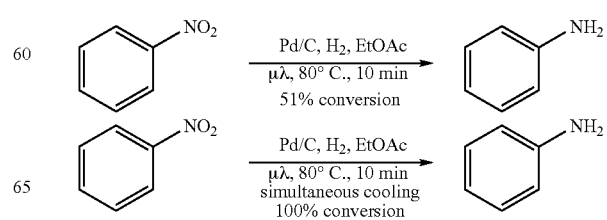

-continued

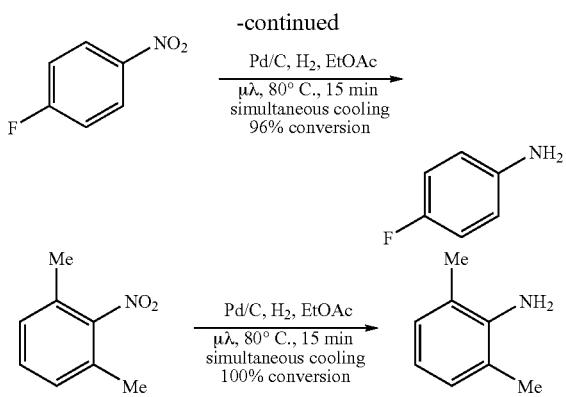

Cbz Deprotection:

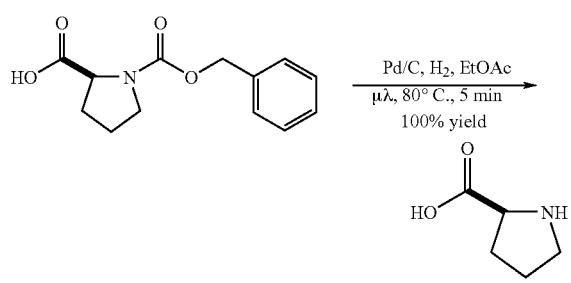

Reductive Amination:

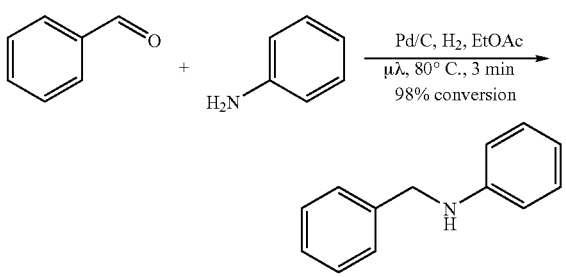

In the drawing, specification, and examples there have been set forth preferred embodiments of the invention, and although specific terms have been employed, they are used in a generic and descriptive sense only and not for purposes of limitation, the scope of the invention being defined in the claims.

The invention claimed is:

1. A method of accelerating organic reactions that include a gas phase reactant, the method comprising:
conducting a hydrogenation reaction selected from the group consisting of olefin hydrogenation, alkyne hydrogenation, carbobenzyloxy deprotection, and reductive amination, using the steps of:
introducing a microwave transparent reaction vessel containing an organic compound to be hydrogenated into a microwave cavity;
purging the reaction vessel containing the organic compound to be hydrogenated;
charging the reaction vessel with hydrogen gas in an amount that is at least stoichiometric with respect to the amount of the organic compound to be hydrogenated;
applying a continuous single mode of microwave radiation within the cavity and to the vessel and the organic compound in the vessel until the organic compound is hydrogenated to a desired yield; and
venting the vessel at the completion of the hydrogenation reaction.

2. The method of accelerating organic reactions according to claim 1 further comprising catalyzing the reaction with a hydrogenation catalyst.

3. The method of accelerating organic reactions according to claim 2 wherein the hydrogenation catalyst is a palladium catalyst.

4. The method of accelerating organic reactions according to claim 1 wherein the step of purging the reaction vessel comprises purging the reaction vessel more than one time.

5. The method of accelerating organic reactions according to claim 1 wherein the step of charging the reaction vessel with hydrogen gas comprises charging the reaction vessel with an amount of hydrogen gas that is greater than stoichiometric with respect to the organic compound to be hydrogenated.

6. The method of accelerating organic reactions according to claim 1 further comprising the step of monitoring the temperature of the reaction vessel.

7. The method of accelerating organic reactions according to claim 1 comprising applying the continuous single mode of microwave radiation within the cavity and to the reaction vessel and to the organic compound to be hydrogenated for a time sufficient to effect a yield of greater than 50% hydrogenation.

8. The method of accelerating organic reactions according to claim 1 comprising applying the continuous single mode of microwave radiation within the cavity and to the reaction vessel and to the organic compound to be hydrogenated for a time sufficient to effect a yield of greater than about 75% hydrogenation.

9. The method of accelerating organic reactions according to claim 1 comprising applying the continuous single mode of microwave radiation within the cavity and to the reaction vessel and to the organic compound to be hydrogenated for a time sufficient to effect a yield of greater than about 90% hydrogenation.

10. The method of accelerating organic reactions according to claim 1 comprising applying the continuous single mode of microwave radiation within the cavity and to the vessel and to the organic compound to be hydrogenated to produce a temperature sufficient to hydrogenate the organic compound to be hydrogenated to the desired yield.

11. The method of accelerating organic reactions according to claim 1 further comprising cooling the reaction vessel during the application of microwave radiation to moderate and control the temperature of the reaction vessel and the organic compound to be hydrogenated.

12. The method of accelerating organic reactions according to claim 1 wherein the step of applying a continuous single mode of microwave radiation within the cavity and to the vessel and to the organic compound to be hydrogenated comprises heating the vessel contents to a temperature of between about 60 and 180° C.

* * * * *